United States Patent
Tykocinski et al.

(12) 
(10) Patent No.: US 6,420,172 B1
(45) Date of Patent: Jul. 16, 2002

(54) METHOD FOR INDUCING TUMOR IMMUNITY

(75) Inventors: Mark L. Tykocinski, Shaker Heights; Joseph Ilan, Cleveland Heights, both of OH (US)

(73) Assignee: TIB Company, LLC, Pepper Pike, OH (US)

( * ) Notice: Subject to any disclaimer, the term of this patent is extended or adjusted under 35 U.S.C. 154(b) by 0 days.

(21) Appl. No.: 07/997,715

(22) Filed: Dec. 31, 1992

Related U.S. Application Data

(63) Continuation-in-part of application No. 07/872,712, filed on Apr. 20, 1992, now abandoned.

(51) Int. Cl.[7] .......................... C12N 5/00; C12N 15/63; A01N 63/00; C07H 21/04
(52) U.S. Cl. .................... 435/375; 435/320.1; 435/455; 424/93.2; 424/93.21; 536/24.5
(58) Field of Search .................... 514/44; 424/93 A, 424/93 B, 93 R, 88, 93.1, 93.2, 93.21; 435/320.1, 172.3, 455, 375; 935/34, 36, 55, 56, 57, 58; 536/24.1, 24.5

(56) References Cited

U.S. PATENT DOCUMENTS 5,045,320 A    9/1991    Mescher ..................... 424/450

FOREIGN PATENT DOCUMENTS

EP    0077571    4/1983
WO    8908667    9/1989

OTHER PUBLICATIONS

Uhlman, 1990. Chemical Reviews 90(4): 543–584.*
International Search Report, Jul. 14, 1993, PCT/US93/03637.
Aaronson, 254 *Science* 1146, 1991.
Antoniades et al., *FASEB J. Abstracts* 4716, 1991.
Berns et al., 52 *Cancer Research* 1036, 1992.
Campbell and Novak, 149 *Journal of Cell Physiology* 293, 1991.
Culouscou et al., 40 *International Journal of Cancer* 646, 1987.
Eppstein et al., 141 *Journal of Cell Physiology* 420, 1989.
Estrov et al., 9 *Journal of Clinical Oncology* 394, 1991.
Fearon et al., 60 *Cell* 397, 1990.
Foekens et al., 63 *Cancer* 2139, 1989.
Foekens et al., 37 *Journal Steroid Biochem. Molec. Biol.* 815, 1990.
Freiss et al., 173 *Biochem. Biophys. Research Communications* 919, 1990.
Gansler et al., 135 *American Journal of Pathology* 961, 1989.
Golumbek et al., 254 *Science* 713, 1991.
Groger et al., 81 *Gene* 285, 1989.
Johnson et al., 115 *J. Cell Biol.* 1991 (Abstract, 15th Intl. Congress of Biochemistry Jerusalem, Israel, 1991), "Regulation of IGF–1 RNA Transcript Levels in rat $C_6$ Glial Cells".
Koenuma et al., 80 *Japanese J. Cancer Res.* 51, 1989.
Korc–Grodzicki et al., *Eighty–Second American Association for Cancer Research Proceedings* vol. 32, Abstract 300, 1991.
Macaulay et al., 50 *Cancer Research* 2511, 1990.
Noguchi et al., 82 *Japanese Journal of Cancer Research* 1199, 1991.
Rodeck et al., 97 *Journal Investigative Dermatology* 20, 1991.
Roholl et al., 16 *Histopathology* 455, 1990.
Theodorescu et al., 148 *Journal of Cellular Physiology* 380, 1991.
Trojan et al., 115 *J. Cell Biol.* 263a, 1991 (Abstract, 1991 ASCB), "Loss of Tumorigenicity of rat Glioblastoma Directed by Episome–Based Antisense cDNA Transcription of Insulin–Like Growth Factor I".
Trojan et al., 115 *J. Cell Biol.* 1991 (Abstract, 1991 FASEB), "Regulation of IGF–1 RNA Transcript Levels in rat $C_6$ Glial Cells".
Trojan et al., 89 *Proc. Natl. Acad. Sci. USA* 4874, 1992.
Walsh et al., 155 *Western J. Medicine* 152, 1991.

* cited by examiner

*Primary Examiner*—Deborah J. R. Clark
*Assistant Examiner*—Shin-Lin Chen
(74) *Attorney, Agent, or Firm*—Foley & Lardner

(57) ABSTRACT

An immunogenic tumor cell, and method for its formation, which includes a tumor cell treated to have an altered intracellular level of a molecular factor compared to an untreated tumor cell.

4 Claims, 3 Drawing Sheets

METHOD FOR INDUCING TUMOR IMMUNITY

Figure 1:
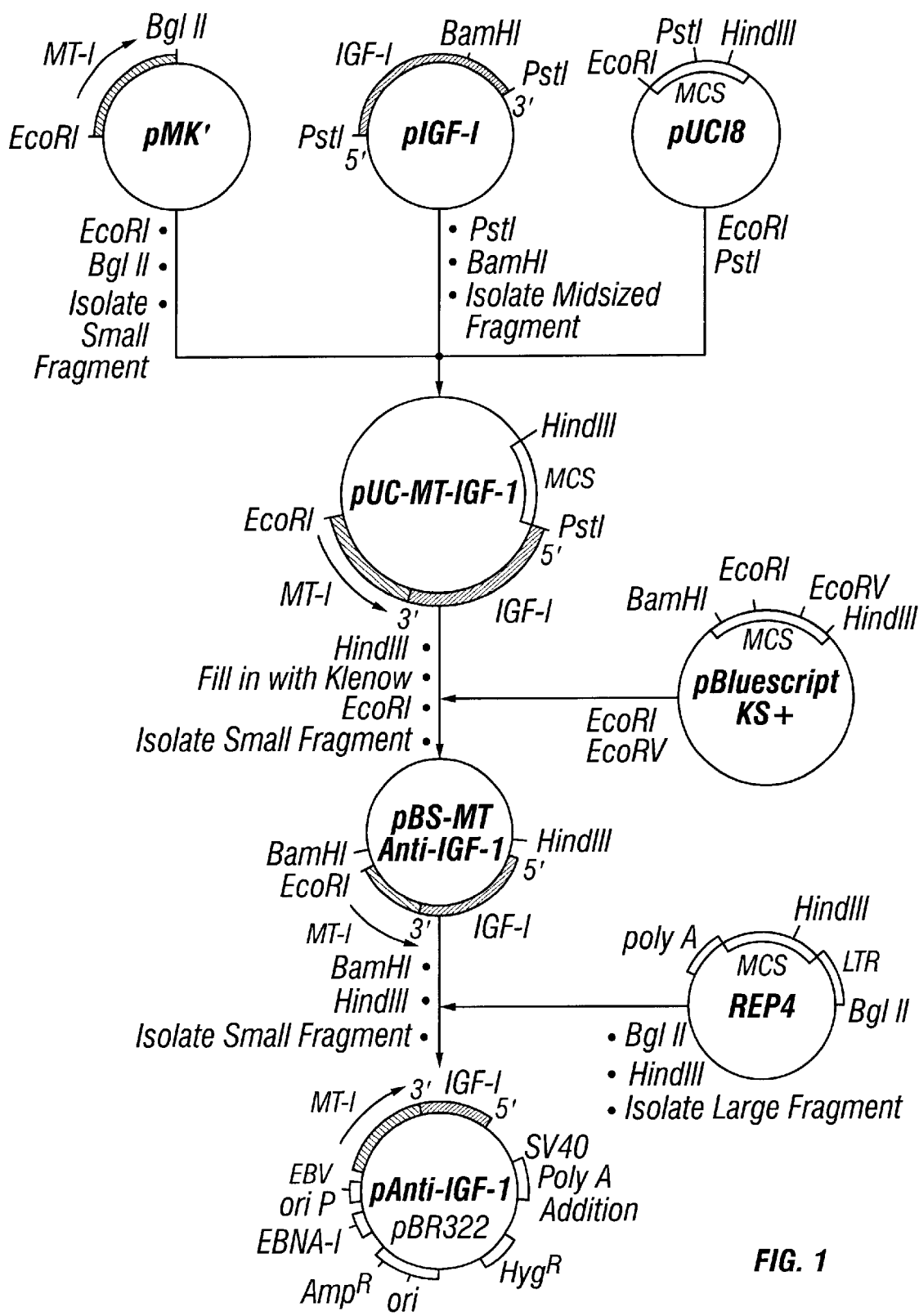

This application is a continuation-in-part of Tykocinski and Ilan, entitled "Method for Inducing Tumor Immunity", U.S. Ser. No. 07/872,712, filed Apr. 20, 1992, now abandoned hereby incoporated by reference herein.

BACKGROUND OF THE INVENTION

This invention relates to methods and reagents for enhancing in vivo tumor cell immunity.

(The following is a general discussion of relevant art and not an admission that any is prior art to the claimed invention. All of the cited or referenced art is hereby incorporated by reference.)

In general, tumors that arise de novo are poorly immunogenic, thereby escaping host antitumor responses (Hewitt et al., 33 Br. J. Cancer 241, 1976). The reasons for this poor immunogenicity are poorly understood. A major objective in the field of tumor immunotherapy is the development of strategies for enhancing tumor immunogenicity, with potential applications in both tumor prevention and cure.

Several experimental strategies have been reported for enhancing tumor immunogenicity, for example, use of mutagen or drug treatment (Van Pel and Boon, 79 Proc. Nat. Acad. Sci. USA 4718, 1982; Frost et al., 159 J. Exp. Med. 1491, 1984; and Frost et al., Maloy and Nicolson (eds.), in "Occult Nodal Metastasis in Solid Carcinoma", Cancer Research Monographs, Vol. 5, New York, Praeger Publishers, 1987); by transfection with a foreign gene encoding an exogenous antigen such as influenza hemagglutinin (Fearon et al., 38 Cancer Research 2975, 1988); by transferring a gene expressing interleukin-2 (Fearon et al., 60 Cell 397, 1990); and by transferring a gene expressing interleukin-4 into a tumor (Tepper et al., 57 Cell 503, 1989, and Golumbek et al., 254 Science 713, 1991).

The role of cytokines and growth factors in tumor cell growth has been discussed in the literature. See, for example, Walsh et al., 155 Western Journal of Medicine 152, 1991; Foekens et al., 63 Cancer 2139, 1989; Koenuma et al., 80 Japanese Journal of Cancer Research 51, 1989; Antoniades et al., FASEB Journal Abstracts 4716, 1991; Aaronson, 254 Science 1146, 1991; Macaulay et al., 50 Cancer Research 2511, 1990; Korc-Grodzicki et al., Eighty-Second American Association for Cancer Research Proceedings Vol. 32, Abstract 300, 1991; Culouscou et al., 40 International Journal of Cancer 646, 1987; Roholl et al., 16 Histopathology 455, 1990; Estrov et al., 9 Journal Clinical Oncology 394, 1991; Rodeck et al., 97 Journal Investigative Dermatology 20, 1991; and Theodorescu et al., 148 Journal of Cellular Physiology 380, 1991. Others have suggested a relationship between receptors for such cytokines and tumorigenicity. See, for example, Noguchi et al., 82 Japanese Journal of Cancer Research 1199, 1991; Campbell and Novak, 149 Journal of Cell Physiology 293, 1991; Foekens et al., 37 Journal Steroid Biochem. Molec. Biol. 815, 1990; Freiss et al., 173 Biochem. Biophys. Research Communications 919, 1990; and Berns et al., 52 Cancer Research 1036, 1992. Yet others have noted that antibodies to such factors may inhibit growth of tumors. See, for example, Gansler et al., 135 American Journal of Pathology 961, 1989, and Eppstein et al., 141 Journal of Cell Physiology 420, 1989. Still others have noted that drugs may inhibit tumor growth. See, for example, Upp et al., 115 American J. Surg. 29, 1988; Hajri et al., 27 Eur. J. Cancer 1247, 1991; Schally 48 Cancer Res. 6977, 1988; and Longnecker, 22 Drug Intell. Clin. Pharmacol. 99, 1988.

Both IGF-I and IGF-II have previously been characterized extensively as growth, and to a lesser extent as differentiation, factors, and are presumed to play significant roles in embryonic and fetal development (see, for example, Froesch et al, 47 Ann. Rev. Physiol. 443, 1985; Whitman et al., 5 Ann. Rev. Cell. Biol. 93, 1989; Spaventi et al., 108 Development 491, 1990; Han et al., 236 Science 193, 1987; Rappolee et al., Spencer EM (ed.), in "Modern Concepts of Insulin-Like Growth Factors", Elsevier Science Publishing Co. Inc., 1991; Shen et al., 83 Proc. Nat. Acad. Sci. USA 9179, 1986). In many instances, cells that express IGF's in embryonic or fetal forms do not continue to express the same cytokine in the adult form to an appreciable extent.

IGF-I and IGF-II are expressed at high levels in a range of tumor cell types (see, for example, Antoniades et al, 50 Intl. J. Cancer 215, 1992; Roholl et al., 16 Histopathology 455, 1990; Williams et al., 61 Mol. Cell Endocrinol. 139, 1989; Foekens et al., 63 Cancer 2139, 1989; Koenuma et al., 80 Jpn. J. Cancer Res. 51, 1989; Culouscou et al., 40 Intl. J. Cancer 646, 1987; Antoniades et al., 5 FASEB J. A1184, 1991; Brunner et al., 16 Breast Cancer Res. Treat. 148, 1990; Brewer et al., 31 Proc. Annu. Meet. Am. Assoc. Cancer Res. A247, 1990; and Macaulay et al., 50 Cancer Res. 2511, 1990). Tumor cells express either one or the other, or both. Also, many tumors express receptors for IGF-I (Rechler et al., 47 Ann. Rev. Physiol. 425, 1985, and Kiess et al., 124 Endocrinology 1727, 1989).

The prior tumor cell literature has focused on the potential role of the IGF's as growth factors driving the proliferation of tumor cells that produce them. In turn, this has led to attempts to inhibit growth of such tumor cells with anti-IGF-I or anti-IGF-II antibodies that are added exogenously. While some growth inhibition has been claimed using anti-IGF-I and anti-IGF-II antibodies in vitro (see, for example, Minuto et al., 48 Cancer Res. 3716, 1988; Huff et al., 46 Cancer Res. 4613, 1986; Blatt et al., 123 Biochem. Biophys. Res. Commun. 373, 1984) and in vivo (Gansler et al., 135 Am. J. Pathol. 961, 1989), tumor development in vivo was not blocked by the anti-IGF antibodies. Similarly, there have been attempts to use octreotide to inhibit growth of tumor cells. While some growth inhibition has been claimed using this agent (see, for example, Hajri et al., 27 Eur. J. Cancer 1247, 1991), tumor development in vivo was not blocked by octreotide.

SUMMARY OF THE INVENTION

Applicant has discovered that the immunogenicity of a tumor cell can be remarkably enhanced by inhibition of expression within that tumor cell of one or more molecular factors that affect a differentiation state (see below regarding how such factors can be readily identified), e.g., cytokines including, but not limited to, insulin-like growth factor I and II (IGF-I and IGF-II), platelet-derived growth factor (PDGF), macrophage colony stimulating factor (MCSF), granulocyte/macrophage colony stimulating factor (GMCSF), and interleukins II and III (IL-II and IL-III); nuclear transcription factors, such as those which bind directly to regulatory sequences in DNA, and other transcriptional factors (e.g., Id), which bind to transcriptional regulators and modulate their transcription regulatory function; other examples include basic helix-loop-helix (bHLH) proteins such as myoD protein, SCL protein, MYC protein, E12, E47, Myf-5 protein, myogenin, and human homologues of the Drosophila genes AS-C, da, h, and emc;

leucine zipper protein, with (bZIP) and without (ZIP) basic domains,: such as Jun proteins, Fos proteins, ATF/CREB proteins; and cell surface receptors associated with differentiation control, erg, estrogen. Methods for identifying other genes whose inhibition enhances tumor cell immunogenicity are defined herein. The best candidate genes are those for which there is evidence that they influence the cell's differentiation state. The phrase "differentiation state" means the molecular repertoire of a cell at a given point in time.

The role of nuclear transcriptional factors as regulators of cellular differentiation states is discussed in the literature. Green et al, 10 *EMBO J.* 4153, 1991. Some of these transcriptional factors bind directly to regulatory sequences in deoxyribonucleic acid and thereby activate the associated gene. Other transcriptional factors, for example, Id, bind to other transcriptional regulators and thereby modulate their transcriptional regulatory function. The expression of nuclear transcriptional factors in both normal and neoplastic cells has been described.

One example of a class of nuclear transcriptional factors linked to differentiation control is helix-loop-helix (HLH) proteins. HLH proteins are defined by virtue of their common HLH domain which spans approximately 60 amino acids and comprises two predicted amphipathic alpha-helices separated by an intervening loop (Murre et al., 56 *Cell* 777, 1989). HLH proteins are able to form either homodimeric or heterodimeric complexes with certain other members of this family, and, as a result, their DNA-binding affinity is modulated. It has been suggested that ubiquitously expressed HLH proteins dimerize with tissue-specific HLH proteins to form a complex that binds with higher affinity to the target sequence (Murre et al., 58 *Cell* 537, 1989). Almost every member of the growing family of HLH proteins has been implicated in transcriptional regulation, oncogenesis, and/or cell type determination and differentiation. See, for example, Jones, 61 *Cell* 9, 1990; Visvader et al., 16 *TIBS* 330, 1991. For example, the HLH protein myoD enforces a myogenic program of differentiation in a variety of cell types. HLH proteins participate in differentiative "decisions" in a highly regulated and cell-specific fashion. See, for example, Howard et al., 110 *Devel.* 1223, 1990; Erickson and Cline et al., 251 *Science* 1071, 1991.

Another example of a nuclear transcriptional factor linked to differentiation control is SCL. SCL is detected in the developing central nervous system, but there is only low level expression in adult brain (Begley et al., 86 *Proc. Nat. Acad. Sci. USA* 10128, 1989). SCL expression is almost exclusively hematopoietic in both human (Green et al., 6 *Oncogene* 475, 1991) and murine (Kouzarides et al., 6 *Oncogene* 195, 1991) tissues. Although SCL is frequently involved in T-ALL, there is no evidence that SCL is normally expressed in the T-lymphocyte lineage. Hence, it has an oncofetal pattern of expression.

A novel subset of HLH proteins have been described that are negative regulators of HLH proteins, such as one that inhibits myoD dependent gene activation (Weintraub and co-workers, 61 *Cell* 49, 1990), as well as ones that inhibit Drosophila HLH's (61 *Cell* 27, 1990; 8 *EMBO J.* 3095, 1989).

In addition to cytokines and nuclear transcriptional regulators, other classes of molecules have been associated with differentiation control. For example, certain cell surface receptors, when engaged by their respective ligands, influence the cellular differentiation state. One example of this is the estrogen receptor. Estrogen is thought to play a role as a differentiation factor on estrogen receptor-positive breast, and perhaps other, for example, pituitary, tumor cells (Fujimoto et al., 82 *Japan J. Cancer Res.* 1436, 1991).

Applicant believes that the absence of expression of such factors, in some manner changes the epitopic phenotype of the tumor cell such that it is immunogenic and recognized by the host immune system, and an immune response can be mounted against that tumor cell. In support of this, applicant has discovered that the introduction of a tumor cell having such a lowered expression into a host animal not only reduces tumor growth, but also the growth of normal tumor cells (i.e., having normal molecular factor expression) within the same host. Indeed, applicant believes that the role of these factors is not solely in growth of a tumor cell (as is implied from the names of some of the factors) but rather in the control of differentiation of such a cell. The influence of the factor in this invention is believed largely due to the factor's effect on a differentiation phenotype which influences tumor immunogenicity rather than the factor's growth modulatory properties.

In contrast to the published art described above, where immunogenicity is enhanced by expression in the tumor cell of a cytokine not normally expressed by that tumor cell, the present invention is based upon the finding that enhanced immunogenicity can be induced in a more optimal fashion by blocking expression in the tumor cell of a factor, such as a cytokine that is normally expressed by that tumor cell. The native factor appears to function in a dominant mode to render the tumor cell non-immunogenic, and hence, inhibition of expression of the factor renders the cell immunogenic.

In view of this discovery, applicant believes that factors that control cellular differentiation states and/or phenotypes may also simultaneously dictate the cell's immunogenic capacity. Applicant has found that tumor cells manipulated to reduce cytokine-expression can be used in immunotherapies to effectively prevent or cure tumors. Immunity induced by such tumor cells is long-lasting and systemic in nature. IGF-I is but one example of a factor that controls tumor immunogenicity; it appears to function as a molecular switch in controlling the immunogenic phenotype of a tumor cell.

Thus, applicant has discovered a broad means by which the antigenicity or immunogenicity of any tumor cell, e.g., solid tumor cells or hematopoietic cells, can be increased by inhibition of expression or activity of one or more molecular factors within that cell. Thus, such cells can be treated to cause a reduction in growth of the tumor within the host, and indeed to cause complete removal of the tumor cells from this host. Given applicant's discovery and the methodology provided below (in which examples of this discovery are provided), it is now straight forward for those in the art to screen any particular target tumor cell to determine whether a reduction in molecular factor expression in that cell will enhance its immunogenicity. In the examples provided below, a preferred method of reducing molecular factor expression is by antisense technology; this technology may be universally applied to all tumor cells and thus immunogenicity to any tumor cell can be induced using a single reagent, e.g., a vector expressing the desired antisense nucleic acid, or its equivalent. Other methods for reducing molecular factor expression can be used, including use of specific antibodies selected to increase immunogenicity of a tumor cell.

Thus, in a first aspect, the invention features an immunogenic tumor cell which includes a tumor cell treated to have a reduced level of a molecular factor compared to an untreated tumor cell.

By "immunogenic tumor cell" is meant a cell which is recognized as a tumor cell by those in the art, and which has been treated in some manner to reduce the level of intracellular molecular factor expression or other cellular molecular factor levels. Such treatment will enhance the immunogenicity of that tumor cell compared to an untreated cell. The terms "molecular factor" and "cytokine" are well understood by those in the art, examples of which are provided above. By "immunogenic" is meant that an immune response is mounted against the tumor cell which allows the host to reduce growth of the tumor cell. Such a property can be measured by techniques well known in the art. Non-limiting examples of tumor cells that may be used in this invention include glioblastomas, sarcomas, thyroid adenomas, breast cancer cells, and small-cell lung carcinomas.

By "reduced level" is meant that the biological activity of the molecular factor is reduced either by reducing the rate of transcription or translation of a gene or mRNA encoding the factor, or by altering the intrinsic activity of the factor itself, e.g., by mutation or by intracellular or other interaction with a chemical agent, including antibodies or specific chemical agents. In some embodiments, the factor may be absent from such cells, or at least detectable at only minute levels.

In related aspects, the invention features a method for producing an immunogenic tumor cell by treating a tumor cell to reduce the level of a molecular factor in that cell; a method for inducing antitumor immunity against an autologous tumor cell in a patient having a cancer cell by reducing the level of a molecular factor to increase the immunogenicity of the tumor cell; a method for inducing anti-tumor immunity against an autologous tumor cell in a patient having such a tumor cell by administering to that patient a heterologous tumor cell of the same tumor type in which the level of a molecular factor has been reduced or inhibited to increase the immunogenicity of those heterologous tumor cells; and a method for inducing anti-tumor immunity against an autologous tumor cell in a patient having such a tumor cell by administering to that patient a tumor cell membrane extract, or isolated proteins thereof, which are isolated or purified from a tumor cell or a heterologous tumor cell of the same tumor type, in which the level of a molecular factor has been reduced or inhibited.

By "autologous" is meant that a tumor cell from the patient to be treated or from another patient having a common major histocompatibility phenotype is used in the method. By "heterologous" is meant that a tumor cell from another patient is used. By "of the same tumor type" is meant that the tumor cell has the same phenotype as that in the patient and was obtained from a patient having a similar cancer. By "membrane extract" is meant an extract of a tumor cell enriched for membranes, but not necessarily containing only membranes. Such an extract is chosen because it will have the antigenic properties necessary to induce an immune response to the tumor cell in vivo. By "isolated proteins" is meant one or more proteins purified to some degree from the extract which still retain the desired immuhogenicity as discussed above. In preferred embodiments, the level of molecular factor is reduced intracellularly.

In yet other aspects, the invention features a method for identifying a molecular factor in a tumor cell which reduces immunogenicity of a tumor cell, by inhibiting expression or activity of that factor in the tumor cell and determining the immunogenicity of the resulting inhibited tumor cell compared to an uninhibited tumor cell; and a method for identifying a reagent (e.g., antisense nucleic acid or ribozyme or antibody) useful for enhancing immunogenicity of a tumor cell by contacting or treating a normal tumor cell with a test reagent and determining whether the treated tumor cell has a greater immunogenicity than the untreated cell.

In an alternative aspect, a similar assay is performed in which the immunogenicity of the tumor cell is not studied, but rather the inhibition of a molecular factor expression (e.g., transcription or translation of the factor) within the tumor cell is studied. This alternative method reduces the amount of in vivo testing required when the immunogenicity of a tumor cell must be evaluated. In particular, it is advantageous to test the inhibition of expression of IGF-I and IGF-II, for example, by identifying those reagents which inhibit transcription of genes encoding IGF-I by use of a fusion gene encoding IGF-I and a readily detectable marker (such as the chloramphenicol acetyl transferase gene).

In preferred embodiments of the above aspects, the methods may include identifying a patient in need of tumor therapy, obtaining a tumor cell from such a patient, culturing the tumor -cell prior to reducing the level of the molecular factor, inhibiting the expression or activity of one or more molecular factors in such a tumor cell or in the cultured tumor cell, and administering a modified tumor cell back into a patient. It is critical only in the invention that a tumor cell in some way be modified to reduce expression or activity of a molecular factor which is recognized to be responsible for a lack of immunogenicity of an unmodified tumor cell, independent of how such methodology may be performed.

In yet other preferred embodiments, the tumor cell is a primary tumor cell or a metastatic tumor cell, and the methods induce tumor regression or prevent tumor recurrence. Examples of tumor cells which might be treated in this method include glioblastoma, neuroblastoma, lung carcinoma, breast carcinoma, osteosarcoma, meningioma, colon carcinoma, squamous cell carcinoma, melanoma, Wilm's tumor, teratocarcinoma and hepatocarcinoma cells.

In a more preferred embodiment of this invention, antisense RNA is used to inhibit molecular factor expression, or equivalent ribozyme technology can be used. In particular, it is preferred to use episomal vectors to produce the antisense RNA or ribozymes, which episomal vectors may include an Epstein-Barr virus (EBV) replicative signal. Alternative vectors, including retroviral and other integrating vectors, may also be used in the invention to express antisense RNA or ribozymes. Antisense oligonucleotides and triple helix forming nucleic acids (e.g. DNA or RNA strands) may also be used in the invention. Additionally, a tumor cell may be transformed or otherwise genetically manipulated to cause the gene encoding a molecular factor to be disrupted or deleted.

In yet other preferred embodiments, a homologous or heterologous tumor cell may be cultured or derived from a cultured cell line derived from either a primary or metastatic tumor cell, and a portion of fragment of the tumor cell used for immunization of the patient, for example, a tumor cell membrane extract or even one or more isolated proteins therefrom.

In those methods suitable for identifying molecular factors which may be inhibited to enhance immunogenicity, it is preferred that the expression of the factor be inhibited by antisense gene transfer in vitro, that the tumor cells after modification be administered to an experimental animal, that the tumorigenicity of the modified tumor cell be determined in that experimental animal, and the ability of the modified tumor cell to induce an anti-tumor immune response then be determined. Thus, it is preferred to use experimental animals which do not have a compromised immune system for these experiments. In these experiments, molecular factor-inhibited and non-inhibited tumor cells may be co-administered or separately administered, and the modified tumor cells may be injected directly into a primary or metastatic tumor site within an experimental animal.

As can be seen from the above description, the invention generally features inhibition of a molecular factor expressed by a tumor to provide a reagent suitable for immunization against such a tumor, either in a prophylactic or treatment procedure, and features methods for identifying the optimal factor to be inhibited within such a tumor cell.

Prior to this invention, applicant believes that no art describes a tumor cell which is modified to reduce molecular factor expression, and is unaware of any art which describes how tumor cell immunogenicity may be enhanced by inhibition of such molecular factor expression. The advantages of this invention are abundant. It is the first time that a reagent has been disclosed which might be used for immunization against tumor cell growth, or tumor cell metastasis, or even as a vaccine against the occurrence of any tumor, for example, in a patient known to be susceptible to one or more types of tumor.

Applicant believes that the inhibition of expression of one or more molecular factors within a tumor cell may enhance the expression of one or more other cell surface molecules, which in turn enhances the immunogenicity of the treated tumor cell. Thus, this invention further features a method for screening for the enhanced expression or increased amount of cell surface factors on inhibited tumor cells. For example, MHC-class I proteins may be enhanced in their expression by increased transcription, or the concentration of MHC-class I proteins may be increased at the cell surface when the amount of molecular factor is reduced within a cell. Other proteins which may be affected include cell surface co-stimulatory molecules or adhesions such as B7, ICAM-I, LFA-3.

Such agents may be screened by standard western or even northern blot analysis. Once such factors are defined applicant recognizes that this provides an alternate means by which tumor cell immunogenicity can be increased, i.e., by providing nucleic acid which encodes those other proteins to cause increased expression of those proteins within a tumor cell, or by administration of those proteins in a manner which will enhance their concentration on a tumor cell surface, for example, by providing a class-I modified MHC having a glycophosphatidyl inositol (GPI) anchor which can be coated onto a tumor cell and that tumor cell then injected back into the patient to provide a vaccine. Proteins that might be useful include not only the MHC-class I and adhesions but also naturally-occurring co-inhibitors whose expression is simultaneously reduced with the expression of molecular factors.

Applicants also note that the inhibition of immunogenicity by molecular factors may be reversed by expressing molecular factor-binding proteins, such as IGF-I binding proteins, which may block molecular factor availability, and thus produce an immunogenic tumor cell. By increasing the level of IGF-I binding protein, the biological activity of IGF-I on the tumor cell is reduced since it interacts with that protein rather than other molecules.

Thus, in another aspect of the invention, the invention features a method for producing an immunogenic tumor cell by reducing the proportion of a biologically active molecular factor that is available to the tumor cell, e.g., relative to other components of the tumor cell surface.

By "biologically active" is meant the activity of a molecular factor which acts to block the immunogenicity of a tumor cell. Thus, this phrase has a broad meaning and includes provision of molecular factor-binding molecules which act to prevent the factor from acting at its normal site on a tumor cell.

In preferred embodiments, the method for reducing includes increasing the amount of a tumor cell component such as a molecular factor-binding molecule which binds to the factor, and thus reduces the biological activity of the factor relative to the tumor cell; and includes contacting the factor with a molecule which blocks the biological action of the factor, such as an antibody. IGF binding protein and/or anti-IGF antibody can be delivered to the intracellular compartment by conjugating the respective protein with a secondary ligand, such as transferrin, that will bind to a cell surface receptor and be internalized into the cell.

Thus, applicant notes that any method by which the activity of a molecular factor in a tumor cell can be reduced (to thereby enhance tumor cell immunogenicity) is within the scope of this invention. Those in the art will recognize that all of the various methods discussed above achieve the same end as one another, that is, the enhanced immunogenicity of a tumor cell, by in some way affecting the expression or activity of a molecular factor in that tumor cell. Given that applicant is the first to recognize that it is the reduced availability of a molecular factor on a tumor cell that is essential to immunogenicity of the tumor cell, applicant has enabled, and is entitled to claims broad enough to cover this concept since those in the art can readily design equivalent methods to produce the same end result using techniques well known in the art.

Down-modulation of molecular factor expression, as a means of enhancing tumor immunogenicity according to the present invention, may be combined with the neo-expression of certain lymphokines, or other immunostimulatory cytokines, to potentiate immunogenicity for certain tumor types. An example of such a lymphokine is interleukin IV. Indeed, applicant believes it appropriate to combine the therapies or methods described herein with other methods to enhance the immunogenicity of a tumor cell. Thus, for example, it is believed useful to, not only inhibit intracellular IGF-1 expression, but to simultaneously add anti-IGF-1 antibody and/or drugs active on IGF-1 levels to obtain the combined effect of these treatments and achieve potential synergistic effects.

Other features and advantages of the invention will be apparent from the following description of the preferred embodiments thereof, and from the claims.

DESCRIPTION OF THE PREFERRED EMBODIMENT

The drawings will first briefly be described.
Drawings
FIG. 1 is a diagrammatic representation of the steps employed to construct the episomal vector pAnti-IGF-I.
FIGS. 2a and 2b are copies of autoradiograms showing induction of antisense RNA transcripts by $ZnSO_4$ in cultured C6 glioma and B-104 neuroblastoma cells. The figure is a composite of several RNA transfer blots. 10 $\mu$g total RNA was used per lane. Molecular sizes (in kb) of the major IGF-I transcripts are shown on the left. FIG. 2a: Lane 1: Parental nontransfected C6 glial cells exposed to serum-free medium.

Lanes 2 and 3: Transfected C6 glioma cells incubated in serum-free medium in the absence (lane 2) or presence (lane 3) of $ZnSO_4$. For lanes 2 and 3, nick-translated rat IGF-I cDNA was used. Lanes 4 and 5: The blot shown in lanes 2 and 3 was rehybridized to nick-translated, human IGF-I cDNA. FIG. 2b: Lane 1: Untransfected B-104 neuroblastoma cells. Lanes 2 and 3: Transfected B-104 neuroblastoma cells incubated in the absence (lane 2) or presence (lane 3) of $ZnSO_4$.

Figure 3:
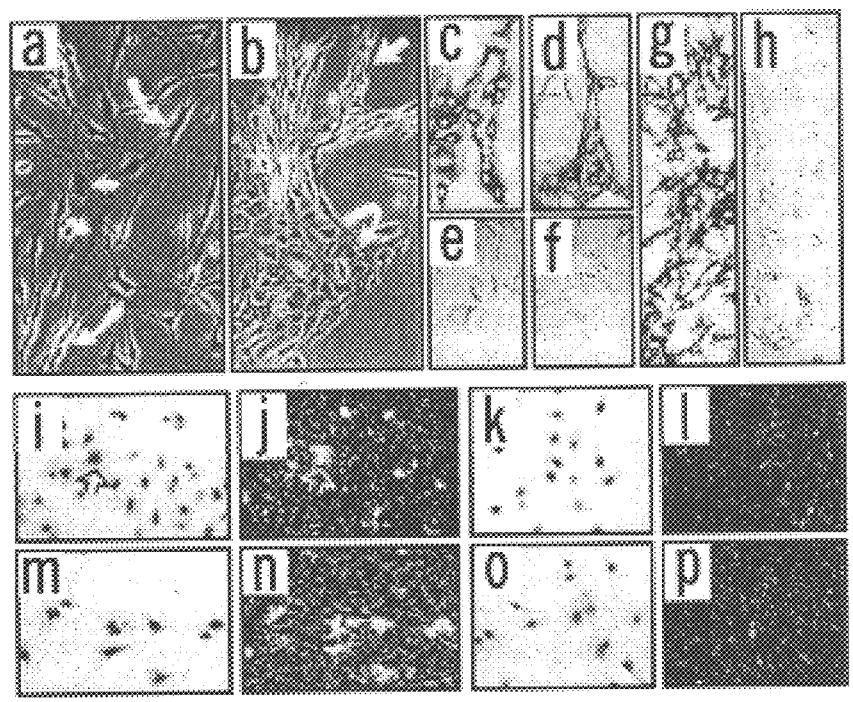

FIGS. 3a–3p are copies of photographs showing localization of IGF-I antisense transcripts and IGF-I protein in C6 glioma parental and transfected cells. FIGS. 3a, 3b: Rat C6 glial cells (FIG. 3a) and B-104 neuroblastoma cells (FIG. 3b) grown in the presence of 0.2 mg/ml or 0.5 mg/ml hygromycin B, respectively, 2 weeks following transfection with pAntiIGF-I. In FIG. 3a, the small arrows indicate the parental population of cells which gradually was eliminated during hygromycin B selection over the course of 2 to 3 weeks. The large arrow represents the stable transfectants which survived the hygromycin B selection. In FIG. 3b, the straight arrow represents the parental population of cells as above, while the bent arrow represents the stable transfectants surviving the hygromycin B selection. (a,b:X 250.) FIGS. 3c, 3d, 3e, 3f, 3g, 3h: Immunocytochemical labelling of cultured cells with antibodies to IGF-I using a quantitative immunoperoxidase technique. FIGS. 3c, 3d: Positively stained parental C6 incubated in the absence (FIG. 3c) or presence (FIG. 3d) of 50 μm $ZnSO_4$. FIGS. 3e, 3f: Negative reaction obtained with B-104 neuroblastoma cells incubated in the absence (FIG. 3e) or presence (FIG. 3d) of $ZnSO_4$. FIGS. 3g, 3h: C6 glioma transfected cells incubated in the absence (FIG. 3g) or presence (FIG. 3h) of $ZnSo_4$. (FIGS. 3c–3f:X250; FIGS. 3g, 3h:X150). FIGS. 3i, 3j, 3k, 3l, 3m, 3n, 3o, and 3p: In situ hybridization of cultured cells with single-stranded $^{35}$S-labeled sense oligonucleotides to detect antisense transcripts. FIGS. 3i, 3j, 3k and 3l: C6 transfected cells maintained in the presence (FIGS. 3i, 3j) or absence (FIGS. 3k, 3l) of $ZnSO_4$. The arrow points out an example of a cell demonstrating a positive signal. In FIGS. 3k and 3l, only background hybridization is apparent. FIGS. 3m, 3n, 3o, and 3p: B-104 transfected cells maintained in the presence (FIGS. 3m, 3n) or absence (FIGS. 3o, 3p) of $ZnSO_4$. FIGS. 3i, 3k, 3m, 3o: bright field; FIGS. 3j, 3l, 3n, 3p: dark field. (FIGS. 3i–3p:X250.) These cells were probed with single-stranded $^{35}$S-labeled IGF sense probe by in situ hybridization.

FIGS. 4a–4k are copies of photographs showing simultaneous localization of IGF-1 antisense transcripts and staining of IGF-1 protein in glioma cells in vitro, and immunocytochemical identification of glioma cells in vivo. FIGS. 4a, 4b: Immunocytochemical labelling of C6 transfected cells with anti-IGF-I antibodies using indirect immunofluorescence technique. Note the presence of IGF-I (FITC fluorescence) in panel FIG. 4a, and absence of fluorescence in cells treated with $ZnSO_4$ in FIG. 4b. The nuclei are counterstained with p-phenylenediamine (ppd) FIGS. 4a, 4b:X250). FIGS. 4c, 4d, 4e: C6-transfected cells maintained in the presence of $ZnSO_4$ for 8–10 hours. FIGS. 4c, 4d, and 4e represent the same microscopic field. Antisense transcripts were localized by in situ hybridization as in FIG. 3, and were then subjected to immunofluorescent labeling of IGF-I protein. The absence of protein (FIG. 4c) is accompanied by a striking in situ hybridization signal localized primarily in the nuclei (FIGS. 4d, 4e). (FIG. 4d, bright field; FIG. 4e, bright field combined with UV lamp.) FIG. 4f, 4g: Mixed culture of C6 glioma parental and transfected cells maintained for 8–10 hours in the presence of $ZnSO_4$. The same microscopic field is visualized in FIGS. 4f and 4g. Cells showing positive immunofluorescent labelling for IGF-I (FIG. 4f, solid arrow) show no detectable signal for IGF-I antisense transcripts (FIG. 4g, solid arrow); whereas cells showing a strong positive signal for antisense transcripts (FIG. 4g, open arrow), presumably the transfected cells, show no detectable fluorescent staining for IGF-I (FIG. 4g, open arrow). See also FIG. 3. (FIGS. 4c–4g: Nuclei are counterstained with p-pd. FIGS. 4h–4k: Histologic sections of injected glioma cells. FIG. 4h: section (hematoxylin and eosin) of a lesion observed at the point of injection of C6 glioma transfected cells, and removed 3 weeks after cell injection. Mononuclear cells, the majority of them plasmocytes and macrophages (asterisk), as well as lymphocytes are observed in the organizing tissue surrounding a few glial cells (arrows). FIG. 4i: Histological section of a small area of a tumor induced by injection of C6 glioma cells (nontransfected). Note dispersed small cells of astrocytic type, some of them forming a pseudorosette (arrow). FIGS. 4h, 4i:X200.) FIGS. 4j, 4k: immunofluorescence staining of glial fibrillary acidic protein (GFA, used for identification of glial cells), in the lesion produced by injection of transfected cells (FIG. 4j), and in the tumor developed after injection of nontransfected cells FIG. 4k). FIG. 4j Note GFA-positive cells (fluorescence,arrow) surrounded by mononuclear cells (visible in FIG. 4h). (FIG. 4k) An area of glioblastoma showing positive reaction with anti-GFA antibodies. Nuclei in (FIGS. 4j, 4k) counterstained with p-pd. (FIGS. 4h, 4i:X200; FIG. 4j:X400; FIG. 4k:X250.)

FIGS. 5a and 5b are copies of photographs of three week tumors derived from C6 glioma nontransfected cells (FIG. 5a) and transfected B104 neuroblastoma cells (FIG. 5b). Arrows indicate the position of the tumors. The rat on the right in (FIG. 5a) was injected with C6 glioma transfected cells and did not develop a tumor over the course of a one-year observation period. Ten rats were observed in this group. Moreover, two additional groups of ten rats each, transfected with antisense IGF-I, were observed for four months and two months, respectively. No rats in either of these groups developed tumors.

INHIBITION OF MOLECULAR FACTOR EXPRESSION

Molecular factors which may be inhibited within tumor cells are generally discussed above, as well as the methodology which might be used for such inhibition. Below are provided examples of methods by which such inhibition of expression can be achieved. Those in the art will recognize that these examples are not limiting in the invention and that many equivalents to such inhibition can be performed by those in the art. In particular, applicant recognizes that reagents other than the antisense reagents described below might be determined by a routine assay in which the level of biological expression of the messenger RNA, or even the level of activity of one or more desired molecular factors, is determined in a tumor cell in response to potential inhibitory compounds. By use of such a procedure, many compounds can be routinely screened in a short period of time. It is particularly advantageous to study the effect of any particular reagent on the level of expression of IGF-I or IGF-II.

Any reagent which lowers the level of expression or the relative amount of such molecular factors can then be tested in an in vivo system, much as described below, by administration of that reagent to a tumor cell to determine whether that reagent will reduce expression of the molecular factor in vivo, and thus enhance immunogenicity of the tumor cell.

Those reagents which are able to perform this function may then be tested to ensure that they do not have significant side effects, and might be used for treatment of patients having tumors.

Suitable antibodies or their equivalent can now be discovered that are suitable for enhancing immunogenicity of a tumor cell. Those in the art will recognize that methods for screening for such antibodies or other reagents are now standard. For example, using the in vivo model described herein, animals having an active immunogenic system can be used to screen tumor cells that have been treated with one or more reagents to determine whether the immunogenicity of the tumor cell has been enhanced by contact with that reagent. Thus, a bank of antibodies specific for reactivity with one or more cytokines can be screened to determine which of those antibodies enhances immunogenicity of the tumor cell. Once such an antibody has been detected, this antibody can be used in vivo or in vitro for treatment of a patient having a tumor cell. Suitable antibodies can be delivered in an unmodified form, or alternatively, antibodies can be conjugated to a secondary ligand, the latter binding to cell surface receptor and allowing for internalization of the antibody into intracellular compartments. Thus, unlike the art discussed above, applicant is not attempting to inhibit growth of the tumor directly by use of specific antibodies against cytokines, but rather is using those antibodies to enhance immunogenicity of the tumor cell, and thus to create a vaccine which can be used in either a prophylactic manner or for treatment of tumor-containing patients.

There follow examples of the invention below. These examples are not limiting in the invention and those of ordinary skill in the art will recognize that many equivalent methods and reagents can be discovered within the scope of the claims.

EXAMPLE 1

Brain Tumor

Malignant gliomas are the most common primary brain tumor, accounting for 29% of all primary brain tumors in humans. The median survival rate is less than one year and the 5 year survival rate is less than 5.5%. The molecular basis of the tumorigenicity of glioma cells has not been defined. Rat glioma cultured cells accumulate high levels of insulin-like growth factor I (IGF-I) transcripts (Johnson et al., 111 *J. Cell Biol.* 505a, 1991, and Kiess et al., 124 *Endocrinology* 1727, 1989). The following experimental system was used to determine whether IGF-I expression is coupled to tumorigenicity. This system is a combined in vivo/in vitro system employing antisense RNA for IGF-I. For this purpose, we assembled an antisense IGF-I expression construct in an expression vector that incorporates Epstein-Barr virus replicative signals and the $ZnSO_4$-inducible metallothionein I transcriptional promoter. Stable glioma transfectants were derived from C6 glioma cells which constitutively express IGF-I. B-104 neuroblastoma cells, derived originally from the same tumor but not expressing IGF-I, were also transfected as controls. In the absence of $ZnSO_4$, the C6 transfectants expressed high levels of IGF-I mRNA and protein as detected by in situ hybridization and immunocytochemistry, respectively. Addition of $ZnSO_4$ in the culture medium resulted in high levels of antisense transcript accumulation, and dramatically decreased levels of endogenous IGF-I mRNA and IGF-I protein. Subcutaneous injection of nontransfected C6 parental cells or C6 cells transfected with a similar vector devoid of the sequences responsible for IGFI-I expression or C6 cells transfected with a similar vector expressing an irrelevant transcript such as growth hormone receptor, into rats resulted in large tumors after 2 weeks, as did both transfected and nontransfected B-104 cells. However, the rats injected with transfected C6 cells yielded no tumors after 32 weeks of observation. A year after injection of the transfected C6 cells a small cyst was apparent in six rats. Histologic sections revealed a few glioma cells infiltrated by a large number of mononuclear cells. No infiltration of mononuclear cells was apparent in the glioma tumors resulting from injection of parental (nontransfected) cells, suggesting that the parental cells, but not the antisense IGF-I transfectants, escape the host immune response.

Materials and Methods

Cell Culture

Rat C6 glioma cells were obtained from the American Type Culture Collection (Rockville, Md.) and cultured essentially as described by Kiess et al., 124 *Endocrinology* 1727, 1989. Briefly, they were maintained in Dulbecco's Modified Eagle's Medium (DMEM; Gibco BRL, Grand Island, N.Y.) supplemented with 15% newborn calf serum (Biologos) for cells maintained in DMEM. B-104 neuroblastoma cells, originating from the same tumor as the C6 glioma line and serving as a control, were obtained from Dr. Lloyd Culp, Department of Molecular Biology and Microbiology, Case Western Reserve University. Culture medium for transfected cells was supplemented with 0.2 mg/ml hygromycin B (Calbiochem) to maintain selection pressure up until 10 days before subcutaneous injection into rats (Male DB-X, age 3 months; $10^7$ cells per injection). 24 hours before injection the cells were washed and maintained in serum-free medium.

Antibodies

Polyclonal antibodies against human IGF-I were provided by the National Hormone and Pituitary Program or obtained commercially from KabiGen (Stockholm). Immunocytochemical localization of IGF-1 by peroxidase was carried out as we described by Trojan et al., 6 *Dv. Neurosci.* 251, 1984. As a positive control, sectioned adult rat liver was employed; as a negative control, human and mouse fibroblast cell lines (HT-1080 and LTK respectively) were employed. The IGF-1 localized immunocytochemically was evaluated semiquantitatively by plotting the "end-points" of staining; these endpoints were defined as maximal dilutions of antibodies still giving a positive reaction in the cells. The endpoint of staining was obtained at a dilution of 1:2000 to 1:3000; the limit of sensitivity occurred at a dilution of 1:100–1:200 (positive nonspecific reaction). The FITC method was carried out by standard procedures using commercially available second antibodies (goat antirabbit) conjugated to FITC. The limit of sensitivity was 1:20–1:30 dilution. For all photographs, the antibody dilution used was 1:400 to 1:500.

Hybridization

In situ hybridization was carried out as described in Boehm et al., 86 *Proc. Nat. Acad. Sci. USA* 656, 1989, and Wang et al., 2 *Mol. Endocrinol.* 217, 1988, except that ethanol was omitted in the prehybridization as well as in the final wash steps. In some experiments a single-stranded oligonucleotide probe, 3'-end-labeled with terminal transferase and $^{35}$S-dATP, was used to score antisense expression. Transfer blot hybridization was carried out as described by Johnson et al., 111 *J. Cell Biol.* 505a, 1991; Johnson et al., 3 *Mol. Endocrinol.* 580, 1989; and Johnson et al., 30 *Mol. Reproduction & Development,* 95, 1991.

Transfection

Transfection of C6 glioma and B-104 neuroblastoma cells was accomplished using Lipofectin reagent (Gibco BRL) according to the supplier's instructions.

Construction of the Episome-based Plasmid, pAntiIGF-I

A diagrammatic representation of the steps employed to assemble the vector is shown in FIG. 1. The pMK' plasmid, containing the mouse MT-I promoter fused to herpes simplex thymidine kinase was provided by Dr. Richard Palmiter (Stuart et al., 81 *Proc. Nat. Acad. Sci. USA* 7318, 1984). pIGF-I harboring a human hepatic cDNA for IGF-1 was provided by Dr. Martin Jansen, Utrecht, The Netherlands (Jansen et al., 306 *Nature* 609, 1983). pUC18 (Yanisch-Perron et al., 33 *Gene* 103, 1985) was provided by Dr. Peter Harte, Department of Genetics, Case Western Reserve University. pBluescript KS+ (Stratagene) was obtained commercially. The construction of REP-4 is described by Groger et al., 81 *Gene* 285, 1989. REP-4 contributes two genes from the Epstein-Barr virus to pAntiIGF-I, the origin of replication (EBV ori-P) and the EBNA-I nuclear antigen, which drives the EBV: ori-P's replicative function. These two genes allow pAntiIGF-I to replicate as an episome. The SV40 polyadenylation signal is present as a termination signal for transcription.

Results

Figure 2:
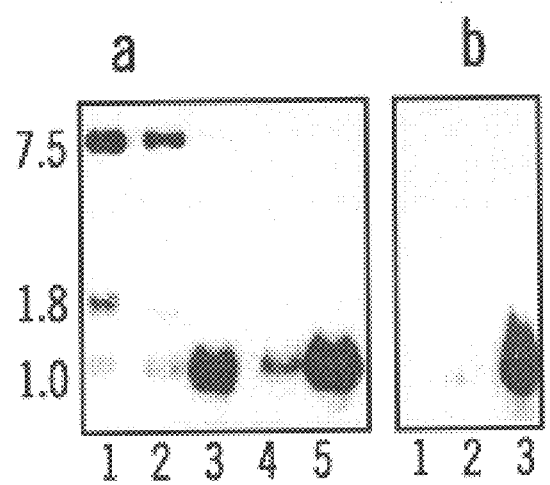

Stable transfectants of C6 glioma cells were derived and were transferred to a serum-free medium for 24 hours. In a serum-free medium, the expression of IGF-I transcripts is greatly enhanced (Johnson et al., 111 *J. Cell Biol.* 505a, 1991). FIG. 2 depicts an autoradiogram obtained from transfer blots of 10 µg total RNA of transfected and untransfected C6 and B-104 cells. FIG. 2a, lane 1, shows untransfected C6 glioma cells exposed to serum-free medium. The pattern of IGF-I transcripts shows prominent bands at 7.5, 1.8 and 1 kb. FIG. 2a, lanes 2 and 3, shows C6 cells transfected with pAntiIGF-I which were exposed to serum-free medium for 24 hours in the absence (lane 2) or presence (lane 3) of 50 µm $ZnSO_4$. Treatment with 50 µm $ZnSO_4$ clearly induces strong expression of the 1 kb antisense transcript, visualized here by virtue of hybridization with double-stranded, nick-translated rat IGF-I cDNA. The induction of antisense by $ZnSO_4$ is accompanied by almost complete disappearance of the endogenous IGF-I transcripts at 7.5 and 1.8 kb. Rehybridization of the same blot with a single-stranded cRNA probe specific for sense IGF-1 mRNA indicated that the endogenous 1 kb transcript also disappeared. FIG. 2a, lanes 4 and 5, show the same blot probed with human nick-translated, double-stranded IGF-1 cDNA. In this case, the endogenous rat IGF-I transcript is not apparent; rehybridization of the blot with a single-stranded cRNA probe specific for antisense transcripts indicated that the 1 kb transcript in Lane 4 was background expression from the MT-I promoter in the absence of zinc. The induced antisense signal is greatly enhanced by use of the human probe. FIG. 2b, lanes 1–3, show an RNA transfer blot from B-104 neuroblastoma cells. Untransfected B-104 cells show no detectable IGF-I transcripts (lane 1), while transfected cells, like C6 cells, show a strong induction of antisense transcripts in cells treated with $ZnSO_4$ (compare lane 3 with lane 2).

Stable transfection resulted in a change in morphology of both C6 glioma cells (FIG. 3a), whose shape appears more elongated in the absence of zinc, and B-104 neuroblastoma cells (3b) whose shape changes from elongate to more irregular and; larger. It is clear that parental C6 cells react positively with antibody to IGF-1 by the immunoperoxidase procedure in the presence (3d) or absence (3c) of $ZnSO_4$. In contrast, B-104 neuroblastoma cells show no staining reaction with the above procedure in the absence (3e) or presence (3f) of $ZnSO_4$, indicating lack of detectable IGF-1 protein in these cells. However, whereas transfected C6 glioma cells showed high intensity staining with anti-IGF-I antibody using immunoperoxidase (3g), in the presence of $ZnSO_4$ the immunostaining disappeared almost completely (3h). Transfected C6 glioma cells were treated with $ZnSO_4$ and probed with labeled human IGF-I single-stranded $^{35}$S-labeled sense nucleotides (to detect antisense transcripts). In situ hybridization showed that transfected glioma cells treated with $ZnSO_4$ express antisense transcripts (3i,j). However, when the transfected glioma cells were grown without $ZnSO_4$ no hybridization signal is apparent, using the same probe at the same specific activity (3k,l). As a control, transfected B-104 neuroblastoma cells gave similar results as described above for the glioma cells. The cells treated with $ZnSO_4$ showed induction of antisense IGF-I (3m,n), while in the absence of $ZnSO_4$ there is no apparent induction (3o,p).

Figure 4:
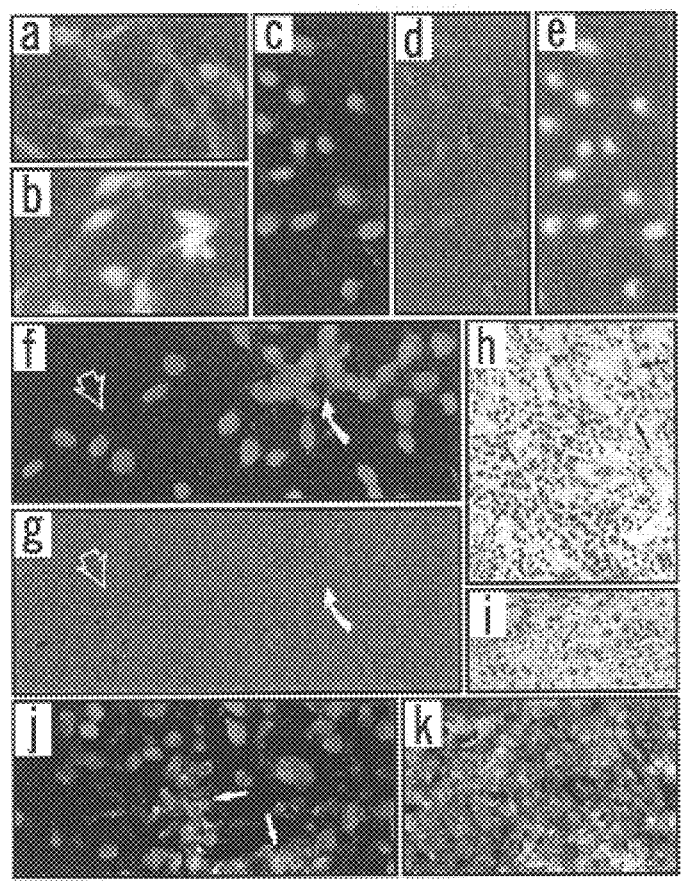

FIG. 4 further demonstrates that induction of antisense IGF-I transcripts results in disappearance of IGF-1 l protein. The immunofluorescence indicating the presence of IGF-1 in transfected cells (4a) disappears when cells are treated with $ZnSO_4$ (4b). FIG. 4(c–e) shows photomicrographs of the same microscopic field in different optical conditions and depicts $ZnSO_4$-treated cells with no immunofluorescent staining (4c). The same cells hybridize strongly to $^{35}$S-labeled sense oligonucleotides (4d) which are localized in cell nuclei (4e). Variation of the position of silver grains with respect to the microscope focal plane accounts for the apparent lack of grains over some cells in 4d,e. Likewise, the presence of photographic emulsion and the necessity to take photographs without the use of a coverslip in FIG. 4e–g introduced variation in fluorescence intensity. FIGS. 4f, 4g show a mixed culture of transfected and parental C6 cells maintained in the presence of $ZnSO_4$ stained for IGF-1 protein (4f) and also hybridized in situ to $^{35}$S-labeled sense oligonucleotides (4g). Thus, both transfected and nontransfected cells were exposed to the same experimental treatments simultaneously. Only transfected cells not showing immunofluorescent staining for IGF-I protein manifest RNA antisense hybridization signals (cf. cells near open arrow which lack the stain seen in the cell cluster and isolated cells near closed arrow).

Southern blots prepared from DNA isolated from C6 transfected cells which were digested with several different restriction endonuclease regimens, were hybridized with $^{32}$P-labeled pAntiIGF-1 and compared with the hybridization patterns derived from similarly treated pAntiIGF-I run on the same gel. The patterns of hybridizing fragments in the DNA from transfected cells were similar to those of the purified plasmid used for transfection, indicating that at least some of the pAntiIGF-I vector DNA was maintained as an episome (data not shown). Such experiments suggested an estimate of 10 copies per cell maintained episomally based on comparison of hybridization signal intensity in cellular DNA to known amounts of purified pAntiIGF-I.

Figure 5:
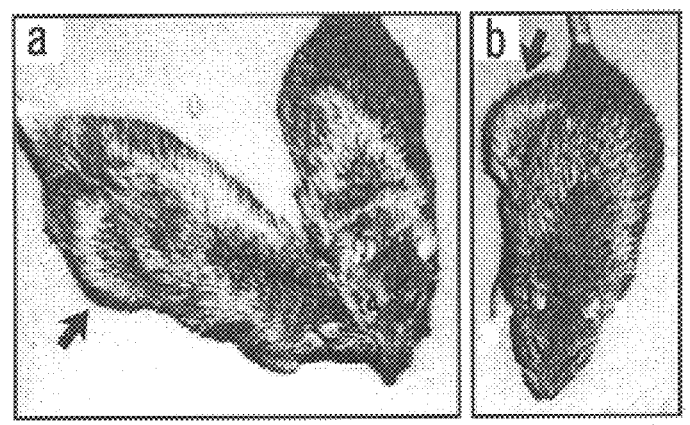

The tumorigenicity of C6 glioma cells is evident in the results shown in FIG. 5. 10 rats were injected subcutaneously with $10^7$ nontransfected C6 glioma cells above the right hind leg. In two weeks, all 10 rats developed a large tumor. An additional 11 rats were injected subcutaneously with $10^7$ transfected glioma cells in the same location. None of the rats injected with transfected cells developed a tumor during the full year of observation (An additional group of rats has been tumor-free for 4 months). The size of the tumor developed 3 weeks after injection of the parental C6 glioma cells is shown in FIG. 5a (arrow) and a representative rat injected with transfected glioma cells is shown on the right.

An additional 5 rats were injected with C6 cells which had been transfected with expression vector which did not contain IGF-I sequences. All 5 of these rats developed tumors after 2 weeks.

As an additional control, B-104 neuroblastoma cells were transfected with pAntiIGF-I. FIG. 5b depicts a rat injected with $10^7$ transfected B-104 neuroblastoma cells as described above. In 2 weeks a large tumor was apparent in all 10 rats injected. An example of a tumor that developed in such a rat is shown in FIG. 5b.

Six out of 11 rats injected with the transfected C6 glioma cells developed a small lesion (<1 cm) at the point of injection a few days after injection. Three were removed for further analysis and the others disappeared after 2–3 weeks. A histological section of one of these lesions, stained with hematoxylin and eosin, is shown in FIG. 4h. It shows a few glial cells (positively identified by immunostaining for glial fibrillary acid protein (GFA) in FIG. 4j) surrounded by an organizing tissue containing many mononuclear cells, mainly plasmocytes and occasionally lymphocyte-like cells. The other two lesions were histologically identical. This suggests that the host immune system reacted against the transfected glioma cells. By contrast, the tumors resulting from injection of non-transfected C6 glioma cells (which stained positively for GFA; FIG. 4k) did not show any apparent infiltration of mononuclear cells within the tumor (4i).

The above shows a combined in vitro and in vivo functional analysis of genetically engineered tumor cells corresponding to antisense phenocopies of a preselected gene. We obtained efficient antisense RNA-mediated inhibition of IGF-I expression in C6 cells using an inducible antisense RNA transcriptional system. An apparent complete shut-off of the protein product was observed following antisense induction in vitro. IGF-I inhibition in vitro resulted in loss of tumorigenicity in vivo.

We demonstrated effective antisense inhibition of endogenous IGF-1 sense transcripts by Northern analysis, and inhibition of protein expression by immunocytochemistry. The latter was linked to antisense expression in the same cells. Of note, antisense IGF-1 transcripts that appeared following $ZnSO_4$ induction were prominently localized to the nuclei by in situ hybridization. This finding tends to support an intranuclear mechanism for antisense RNA-mediated inhibition.

The use of stable antisense transfectants allows analysis of their phenotypic (including tumorigenic) properties both in vitro and in vivo, and provides an in vitro/in vivo assay system suitable for screening transformation potential genes.

The mechanism underlying the loss of tumorigenicity for the antisense IGF-1 transfectants is linked to enhanced immunogenicity. Applicant notes a striking infiltration of mononuclear cells surrounding the injected C6 transfected cells in vivo. No such infiltrates ere apparent for the parental (IGF-I positive) cells in he tumors formed in vivo. This indicates that the loss of tumorigenicity may be due, at least in part, to an enhanced host immune response to the IGF-I negative cells. This possibility is substantiated by the examples provided below. This immunological component may exist together with an antiproliferative effect. C6 cellular proliferation is likely to involve factors in addition to IGF-1, however, since the rate of incorporation of $^3H$-thymidine into transfected C6 cells cultured for 48 hours in serum-free medium was unaffected by the presence of $ZnSO^4$ or IGF-I protein (50 µg/ml) in the culture medium (data not shown).

Example 2

Tumor Protection Experiments

In order to determine whether transfected (antisense IGF-I) glioma cells can elicit an immune response against parental (nontransfected) glioma tumor in vivo, several experiments were carried out. In a first set of experiments, $10^7$ parental glioma cells were injected subcutaneously above the left hind leg of ten rats. Three weeks later, once a large tumor was evident in each of the injected rats, a second injection was given subcutaneously above the opposite hind leg. This second injection included $10^7$ transfected (antisense IGF-I) glioma cells. Within three weeks, there was a complete disappearance of the tumors in all ten rats. In all controls, including rats secondarily injected with glioma cells stably transfected with episomes devoid of antisense IGF-I transcriptional cassettes, tumors persisted and after two months grew to sizes necessitating sacrifice of the animals. These results were confirmed in three separate experiments.

A second set of experiments further addressed the ability of transfected (antisense IGF-I) glioma cells to cure preexisting glioblastoma. Tumors were established in ten rats as described above, and after three weeks (when a large tumor was evident in each of the ten animals), tumors were surgically excised from all animals. These animals were then divided into two groups. The first group of five animals did not receive any further treatment. In all of them, there was local recurrence of tumor after approximately three weeks, reflecting the incomplete excision of the tumor. The second group of five animals received an injection of $10^7$ glioma cells transfected with the episome described above. None of these rats showed signs of tumor recurrence at the excision or other sites. The findings were validated in three separate experiments.

During the phase of tumor involution in each of the experiments above, histologic analyses showed that tumors were abundantly infiltrated with mononuclear cells. Immunocytochemistry showed that between 60–70% of the infiltrating cells were $CD8^+$ lymphocytes. The remainder of the infiltrating cells consisted of macrophages and $CD4^+$ lymphocytes.

In a third experiment, we turned from tumor cure to tumor prevention. Ten rats were injected subcutaneously above the left hind leg with $10^7$ parental glioma cells and simultaneously above the right hind leg with $10^7$ transfected (antisense IGF-I) glioma cells. No tumors developed in any of the rats, whereas when only parental glioma cells were injected at the secondary site, a large tumor developed in each of the rats after three weeks at both sites. Furthermore, when glioma cells transfected with a control episome (devoid of the IGF-I component) were injected at the secondary site into five rats, all developed tumors. An additional control consisted of six rats injected with $10^7$ glioma cells stably transfected with an analogous episome in which the IGF-I sequence was replaced by a full-length rat growth hormone receptor cDNA in the sense orientation. All six animals developed abnormally large tumors. Hence, the protective effect is specifically associated with tumor cells expressing antisense IGF-I which thereby elicit a host immune response against parental glioma cells, as well as against themselves.

The specificity of the host anti-tumor immune response was demonstrated in a fourth set of experiments. First, transfected (antisense IGF-I) and parental glioma cells were mixed together, and the cellular mixture was co-injected above the left hind leg of ten rats. No tumor developed in any of the animals for a full year of observation. A small cyst developed at the injection site in three of the animals; two of them were surgically removed for histologic examination and the third disappeared after a short while. The cyst consisted mainly of lymphoid mononuclear cells, of which 80–90% were CD8$^-$ lymphocytes.

A second tumor cell mixing experiment was performed, in this case combining transfected (antisense IGF-I) neuroblastoma cells and parental glioma cells. After three weeks, a large tumor developed in all five rats so injected. The tumors were removed, and histological examination in each case showed a mixed tumor consisting of neuroblastoma as well as glioma cells. This was confirmed by immunocytochemistry.

A third tumor cell mixing experiment consisted of the injection of a combination of transfected (antisense IGF-I) glioma cells and transfected (antisense IGF-I) neuroblastoma cells into five rats. After three weeks, all animals developed large tumors which histologically proved to be composed solely of the neuroblastoma component.

These experiments together establish that the host immune response induced by transfected (antisense IGF-I) glioma cells is specific for glioma cells and can distinguish between glioma and neuroblastoma components in a mixed tumor. Furthermore, this indicates that nonspecific bystander effects mediated by other immune cells, such as natural killer cells, are not essentially responsible for tumor regression.

In conclusion, we have unequivocally demonstrated that inhibition of IGF-I expression in glioma cells elicits a highly immunogenic phenotype in these tumor cells. This immunogenicity can be used not only for purposes of tumor prevention, but also for eradication of pre-existing tumor at distal sites. Furthermore, the host immune response appears to consist predominantly of CD8$^+$ lymphocytes. This host immune response is highly specific for the immunogenic tumor cell type used, and in fact, it can distinguish between different tumor cell types (IGF-I$^+$ and IGF-I$^-$) admixed in a combined tumor at a single site.

These findings are consistent with the notion that IGF-I functions as a dominant cytokine in defining not only the differentiation, but importantly, also the immunogenic phenotype of glioma cells. A critical event in tumorigenesis may well be an IGF-I-driven phenotypic change which confers upon certain tumor types the capacity to escape the immune system. The present invention discloses that inhibition of IGF-I in such tumors can induce a highly immunogenic phenotype. Since some tumors express IGF-II instead of IGF-I, it is anticipated that in such tumors, inhibition of IGF-II will allow for an analogous induction of an immunogenic phenotype. The present invention also provides for an efficient coupled in vitro/in vivo assay system for determining which other cytokines in any tumor type are responsible for down-modulating tumor immunogenicity.

To establish whether treatment by IGF-I antinsense-transfected cells was effective against glioblastomas established in the brain, we injected a group of rats intracranially with 1×10$^6$ to 2×10$^6$ parental or transfected C6 cells. After 1 week several rats were sacrificed and their brain tissue prepared for histopathological examination. Of the remaining rats, six of six that had been injected with IGF-I antisense transfected cells have survived 4 months with no evidence of tumor development whereas five of five injected with parental cells either died after 3 to 4 weeks or were sacrificed when tumor growth was evident at the point of injection. A second group of six rats was injected intracranially with 1×10$^6$ to 2×10$^6$ parental cells and, 2 to 3 days later, injected subcutaneously above the right hind leg with 10$^7$ transfected cells. These rats have all remained tumor-free for 4 months. During tumor involution in the brain, abundant filtration of mononuclear cells, predominately CD8$^+$ lymphocytes, was observed (as was the case for involuting subcutaneously tumors). These experiments are described in the accompanying appendix, (Trojan, et al, Treatment and Prevention of Rat Glioblastoma by Immunogenic C6 Cells Expressing Antisense Insulin-Like Growth Factor I RNA, to be published in Science 259: 94–97, Jan. 1, 1993) the whole of which, including drawings, is hereby incorporated by reference and made a part of this application.

Assay for Inhibitors of Molecular Factor Expression

As discussed above, inhibitors other than antisense molecules described above can be discovered using methodology equivalent to that described above. For example, inhibition of expression of any of those molecular factors noted above, or other factors, can be performed using the antisense technology described above in similar assay systems. Any inhibition of molecular factors which improves immunogenicity will define a molecular factor that can be usefully inhibited in its expression or activity in this invention. In addition, antibodies or other specific drugs which affect activity of molecular factors may be assayed using similar methodology.

As described above, those in the art will recognize that any methodology which will reduce the activity of molecular factors within a tumor cell or on the tumor cell surface or which acts in a similar manner, such as, for example, by increasing the availability of other agents which may block molecular factor action, may be discovered using routine procedures. The basic concept that has been described by applicant is that tumor cell immunogenicity can be enhanced by reduction of relative molecular factor levels. Once this is recognized, those of ordinary skill in the art can readily assay the relevance of other components using routine procedures to determine which components of a tumor cell are linked to immunogenicity via their effect on cytokine concentrations. All of these components are within the scope of this invention, including the methods which might be used to define such components.

Cellular Fractionation

While applicant has demonstrated that whole tumor cells can be used for immunization of animals in vivo, applicant also recognizes that portions of such cells may be used as the immunogenic agent. For example, the cells may be fractionated using standard procedures to isolate cell surface components such as those present on a cell membrane and those cell membranes or even isolated proteins or protein fractions therefrom can be used to immunize animals in vivo. Those of ordinary skill in the art will recognize that methodology for determination of active membrane fractions are well known in the art and need not be further elaborated upon here. In addition, applicant recognizes that the administration of live tumor cells, even though immunogenic, may be resisted by some in the art. Thus, the invention also features inactivated immunogenic tumor cells, for example, those which have been inactivated for agents such as irradiation, emetine, or mitomycin C treatment prior to use as cellular immunogens. Methods for inactivating the proliferation capacity of tumor cells are well known by those in the art and are equally applicable in this invention.

According to one embodiment of the present invention, a plasma membrane fraction is prepared from a tumor cell population in which the expression of the relevant cytokine has been inhibited. Such plasma membrane fractions are prepared either from living cells or from irradiated cells. These fractions are further treated with DNAse to totally digest all residual cellular and plasmid DNA. Methods for preparing plasma membrane fractions from cells are well known to those familiar with the art.

According to one such method, plasma membranes are isolated by a modification of the procedure of Aronson and Touster (Aronson and Touster, 31 *Meth. Enzymol.* 90, 1974). The cells are homogenized in TMK buffer containing 0.25 M sucrose, and the homogenization is carried out by using a loosely fitted dounce homogenizer. Since most of the plasma membrane fraction is in the microsomal pellet (60%), only the latter is processed and the nuclei are discarded. The percentage of plasma membrane in the microsomal fraction is determined from the activity of 5'-nucleotidase. The plasma membrane is purified from the microsomal fraction by a discontinuous sucrose gradient as described in said publication.

Drugs

As cited above, preferred embodiments of the present invention include those in which gene sequences are used to inhibit expression of IGF's or other relevant cytokines in tumor cells to render them immunogenic. However, it is clear that having taught that IGF's and other cytokines function as molecular switches to control tumor immunogenicity, other therapeutically relevant strategies can be devised for inhibiting the expression of these cytokines or other molecular factors in order to enhance tumor immunogenicity. According to one such alternative embodiment of the present invention, drugs are used which function as transcriptional inhibitors of the molecular factor-encoding genes. Such drugs can be used either in vitro or in vivo. When used in vivo, said drugs shut off the production of molecular factors in all tissues in the body, including the tumor cells (which would thereby be rendered immunogenic). Since the immunogenic effect will be evident within the first two to three weeks, long term drug administration of the drug would not be necessary. Moreover, the short-term inhibition of molecular factor expression in normal tissues is not expected to pose a significant toxicity problem. Blocking IGF-I production by liver will not be toxic since the liver produces it for export and other tissues do not require this cytokine for survival.

There are well-established experimental methods for identifying drugs that can function as transcriptional blockers for specific genes. For example, if the goal is to identify IGF-I transcriptional inhibitors, one can link the IGF-I promoter/enhancer element, which has already been cloned, to a reporter gene. One such reporter gene is the gene encoding beta-galactosidase which is a sensitive and easily assayable marker. Tumor cells can be stably transfected with this construct, cultured in 96-well plates under conditions in which the promoter is expressed constitutively and the reporter protein product is detectable by a color reaction. Large panels of drugs can be readily screened by adding them to the cells and screening for loss of beta-galactosidase activity. It should be apparent to those familiar with the art that a broad set of similar assays could be devised.

Molecular Factor-Binding Proteins

According to yet another embodiment of the present invention, IGF-I or other molecular factors can be inhibited in tumor cells in order to render them immunogenic by manipulating IGF-binding protein expression. For example, one can transfect into the tumor cells a transcriptional cassette encoding an IGF-binding protein that functions to bind and thereby inactivate the cytokine. Use of episomal expression vectors for this purpose permits a large excess of IGF-binding protein production. Alternatively, some IGF-binding proteins have been reported to stimulate IGF-I activity. Therefore, episome-based transcriptional cassettes expressing antisense to such proteins could be used to suppress IGF-I activity. Similar strategies can be devised for other molecular factors where binding proteins are known or will be found to play a significant role in modulating molecular factor function.

Nucleic Acid Inhibit ion Methods

Gene sequences other than antisense sequences can be used to inhibit IGF-I expression in tumor cells in a gene-specific fashion. For instance, the 5'-untranslated region of human IGF-I includes a sequence of twelve nucleotides which lends itself as a target for triplex formation. In fact, according to the current state of the art, this particular sequence provides a best fit for triplex formation. Two alternative approaches can be used for achieving triplex formation in this context and thereby gene-specific transcriptional inhibition. One approach is to use oligonucleotide DNA sequences, according to standard procedures. DNAse activity can optionally be incorporated into these sequences. A second approach entails the use of RNA sequences that will form triplexes with the double-stranded DNA targets To this end, an episome-based transcriptional cassette which encodes the specific RNA sequence which binds the twelve base pair IGF-I target DNA sequence and inhibits IGF-I expression can be used. Of course, the chromosomal target sequences can vary in length and position.

Another example of a gene sequence to be used for molecular factor transcriptional inhibition is a ribozyme sequence. Strategies for devising such sequences for specific gene inhibition are well known to those familiar with the art.

Yet another example of a gene sequence to be used for developing tumor cell derivatives that are blocked in molecular factor expression is the use of sequences that can be employed for gene knockout by homologous recombination. Once both chromosomal copies of the molecular factor gene have been knocked out by such a method, the tumor cell can be used as a tumor immunogen. Alternatively, somatic gene replacement on both chromosomes, or somatic gene mutation on both chromosomes, can be applied.

Use

The methods described above can be performed as described above or by equivalent means. The inhibitory molecules, membranes or tumor cells useful in this invention can be administered to a human or other primate by standard procedures, e.g., by retroviral or naked DNA insertion into a tumor tissue in vivo, or by in vitro treatment of a tumor cell. Those in the art will recognize that appropriate dosages and administrative protocols can be determined by standard procedures.

For example, the primary solid tumor can be removed surgically and placed into standard growth media. The tumor tissue will be minced into small pieces and then treated with trypsin, collagenase or both, according to methodologies will known in the art. Cells will be propagated in short term culture to permit recovery from the enzymatic treatment. Subsequently, cells will be transfected with 20 micrograms of circular episome-based vectors (per $10^7$ tumor cells) carrying the antisense IGF-I RNA or IGF-II transcriptional cassette, or any other antisense cassette corresponding to a molecular factor shown by the in vitro/in vivo assays disclosed in the present invention to be essential for blocking tumorigenicity by invoking the immune system. Stable transfectants will be derived according to well-established protocols (see, for example, Hambor et al., 85 *Proc. Nat. Acad. Sci. USA* 3555, 1988). The patient will be injected subcutaneously with $10^8$–$10^9$ stably transfected tumor cells. Alternatively, the stably transfected tumor cells will be irradiated according to standard protocols prior to injection.

Another embodiment of the present invention entails the preparation of isolated tumor cells to be cultured in vitro as described above. In this case, antisense IGF-I or antisense IGF-II oligonucleotides, or IGF-I specific ribozymes, will be added to the tumor cells in vitro. Inhibition of IGF expression will be documented by immunocytochemistry and Northern RNA blot analysis. Once inhibition has been confirmed, the tumor cells will be injected subcutaneously as described above.

Other embodiments are within the following claims.

What is claimed is:

1. A method for inducing an anti-tumor immune response against a tumor cell in a patient comprising:

administering to said patient having said tumor cell a heterologous tumor cell of the same tumor type wherein one said heterologous tumor cell has a reduced intracellular level of IGF-I relative to the level of IGF-I normally expressed in said heterologous tumor cell, and wherein said reduction in the intracellular level of IGF-I results in said heterologous tumor cell inducing an anti-tumor immune response when administered to said patient.

2. A method for inducing an anti-tumor immune response against a tumor cell in a patient comprising:

administering to said patient having said tumor cell a autologous tumor cell of the same tumor type wherein one said autologous tumor cell has a reduced intracellular level of IGF-I relative to the level of IGF-I normally expressed in said autologous tumor cell, and wherein said reduction in the intracellular level of IGF-I results in said autologous tumor cell inducing an anti-tumor immune response when administered to said patient.

3. The method of claim 1 wherein prior to said administering, the expression of a nucleic acid encoding IGF-I is inhibited in said heterologous tumor cell in vitro.

4. The method of claim 2 wherein prior to said administering, the expression of a nucleic acid encoding IGF-I is inhibited in said autologous tumor cell in vitro.

* * * * *